United States Patent [19]

Murphy et al.

[11] 4,178,222

[45] Dec. 11, 1979

[54] SOLID ELECTROLYTE OXYGEN SENSOR WITH ELECTRICALLY ISOLATED HEATER

[75] Inventors: Michael P. Murphy; Raymond D. Willis, both of Flint, Mich.

[73] Assignee: General Motors Corporation, Detroit, Mich.

[21] Appl. No.: 892,642

[22] Filed: Apr. 3, 1978

[51] Int. Cl.² .................................................. G01N 27/46
[52] U.S. Cl. .................................. 204/195 S; 338/271
[58] Field of Search .............................. 204/15, 195 S

[56] References Cited

U.S. PATENT DOCUMENTS

| | | | |
|---|---|---|---|
| 2,030,937 | 2/1936 | Reichmann | 123/145 A |
| 2,898,571 | 8/1959 | Moule et al. | 338/238 |
| 3,252,122 | 5/1966 | Baxter | 338/271 |
| 3,546,086 | 12/1970 | Sayles | 204/195 S |
| 3,616,274 | 10/1971 | Eddy | 204/1 S |
| 3,815,560 | 6/1974 | Wahl et al. | 123/117 R |
| 3,844,920 | 10/1974 | Burgett et al. | 204/195 S |
| 3,915,828 | 10/1975 | Cleary et al. | 204/195 S |
| 3,928,161 | 12/1975 | McIntyre et al. | 204/195 S |
| 3,999,947 | 12/1976 | Mihara et al. | 23/254 E |

FOREIGN PATENT DOCUMENTS 2131365 11/1972 France.
1367389 9/1974 United Kingdom.

Primary Examiner—T. Tung
Attorney, Agent, or Firm—Robert J. Wallace

[57] ABSTRACT

A readily manufacturable heated solid electrolyte oxygen sensor. The sensor includes an elongated heater supported on a tubular reference electrode terminal in desired position relative to a solid electrolyte member within a cylindrical housing. The heater and terminal form a mutually electrically isolated subassembly in which the heater is in predetermined disposition with respect to the solid electrolyte member. An elongated heater is disposed within one or more ceramic sleeves that are in turn disposed within the electrode terminal tube. The heater, sleeves, and the terminal tube are vitreously bonded together to form a subassembly.

6 Claims, 4 Drawing Figures

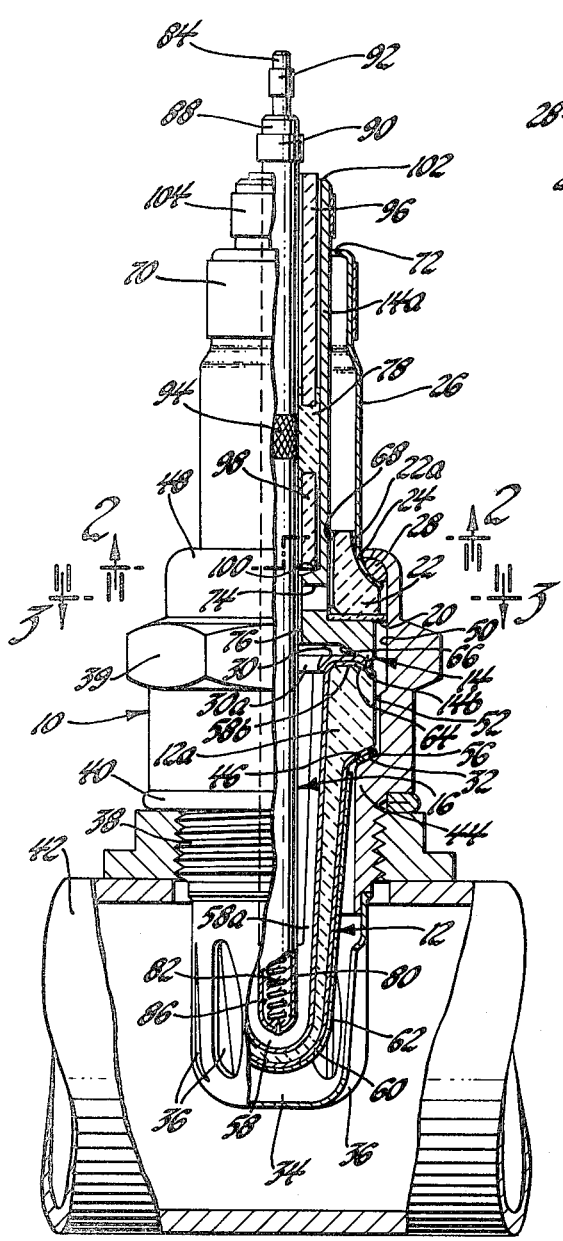

SOLID ELECTROLYTE OXYGEN SENSOR WITH ELECTRICALLY ISOLATED HEATER

BACKGROUND OF THE INVENTION

This invention relates to a heated galvanic-type solid electrolyte oxygen sensor, and more particularly to an improved and readily assemblable construction of such a sensor in which the heater is electrically isolated from sensor terminals.

Solid electrolyte galvanic oxygen sensors essentially include an oxygen-ion-conductive ceramic body with porous electrodes on opposite faces of the body. One electrode is exposed to a reference source of oxygen. The other electrode is exposed to a source whose oxygen content is to be measured. A difference in oxygen partial pressure at the electrodes results in a corresponding electrode potential difference, providing a sensor output voltage.

The output voltage of such sensors can be used to measure oxygen or unburned combustibles in combustion gases produced by an internal combustion engine. This voltage can be used in monitoring and controlling the combustion process, as disclosed in U.S. Pat. No. 3,616,274 Eddy, U.S. Pat. No. 3,844,920 Burgett et al and U.S. Ser. No. 787,900 Howarth, filed Apr. 13, 1977, now U.S. Pat. No. 4,129,099.

The solid electrolyte of such a sensor must be heated to an elevated temperature to obtain an appreciable output voltage. Also, sensor output voltage varies directly with changes in temperature, especially at lower operating temperatures. Combustion gases can be used to heat the sensor to operating temperatures but such gases vary widely in temperature, particularly when from an internal combustion engine. The aforementioned U.S. Pat. No. 3,616,724 Eddy discloses sensor temperature compensating means that includes a surrounding resistance heater. U.S. Pat. No. 3,815,560 Wahl et al discloses a surrounding resistive heater to maintain an electrolyte tube at high temperatures where its output voltage is least affected by temperature change. The aforementioned U.S. Ser. No. 787,900 Howarth now U.S. Pat. No. 4,129,099 discloses doping the solid electrolyte with iron oxide for temperature compensation. It additionally discloses disposing a resistance heater inside a solid electrolyte tube for maintaining the sensor at higher operating temperatures and for supplemental heating on start up.

For automotive applications, the heated sensor should be particularly rugged and reliable. In addition, for higher reliability and lower cost, the heated sensor should be simple and readily manufacturable. U.S. patent application Ser. No. 892,644 entitled "Heated Solid Electrolyte Oxygen Sensor", concurrently filed herewith in the name of Michael P. Murphy, a co-inventor herein, discloses a new way to incorporate a heater in the oxygen sensor, particularly an automotive oxygen sensor. His invention involves forming a subassembly of the heater and the sensor reference electrode terminal. In the subassembly, the heater is prealigned so that when the reference electrode terminal is assembled with its solid electrolyte, the heater is also inherently aligned with the solid electrolyte. In summary, Murphy proposes adding a heater to a solid electrolyte oxygen sensor as a subassembly with a reference electrode terminal for the solid electrolyte. The heater-electrode terminal subassembly is particularly useful in an oxygen sensor such as disclosed in U.S. Pat. No. 3,844,920 Burgett et al.

One specific construction for insulatingly supporting and aligning a heater with a reference electrode terminal is shown in FIGS. 5-8 of the aforementioned U.S. patent application Ser. No. 892,644, but not specifically claimed therein. This specific construction is not suggested by other embodiments described in U.S. patent application Ser. No. 892,644 or the invention claimed therein.

In this specific construction, the heater is electrically isolated from the electrode terminal. Moreover, the heater is not only supported in aligned disposition on the electrode terminal but precise alignment is assured, even though the components are readily assemblable. This construction includes use of a vitrified bond to secure the subassembly components together. A vitrified bond has reportedly been previously used in making electrically insulated coaxial transformer thru-the-wall connectors. We have found that a vitrified bond can provide a simple, rugged, reliable and readily manufacturable subassembly for a heated oxygen sensor. In addition, the heater in the resultant sensor is coaxial. All terminals are coaxial. Further, the heater is electrically isolated from the sensor electrodes. Hence, the heater can be controlled independently from sensor electrodes. Such a sensor is an improvement on the invention claimed in the aforementioned U.S. patent application Ser. No. 892,644.

OBJECTS AND SUMMARY OF THE INVENTION

It is, therefore, an object of this invention to provide an improved heated solid electrolyte galvanic sensor, and more particularly an improved heater-reference electrode terminal subassembly.

A further object of this invention is to provide a simple, rugged, reliable and readily manufacturable solid electrolyte oxygen sensor having a heater-reference electrode terminal subassembly in which the heater is electrically isolated from the reference electrode terminal.

Another object of this invention is to provide an improved method of making a heated solid electrolyte galvanic sensor having a mutually electrically isolated heater-reference electrode terminal subassembly.

These and other objects of the invention are attained in a solid electrolyte galvanic oxygen sensor having a heater supported on a tubular reference electrode terminal in a desired predetermined concentric relationship with respect to the sensor electrolyte member. The heater and terminal comprise a subassembly readily assemblable with the electrolyte member and a surrounding metal housing. The heater is supported by a vitrified bond within at least one ceramic sleeve that is in turn supported by a vitrified bond within the tubular portion of the reference electrode terminal. Means coacting with terminal and housing flanges hold the electrolyte member, heater-terminal subassembly and housing in a fixed predetermined concentric relationship.

BRIEF DESCRIPTION OF THE DRAWINGS

Other objects, features and advantages of the invention will become more apparent from the following description of the preferred embodiment thereof and from the drawings, in which:

FIG. 1 is an elevational view in partial section showing an embodiment of an oxygen sensor made in accordance with this invention;

FIG. 2 is a sectional view along the line 2—2 of FIG. 1;

FIG. 3 is a sectional view along the line 3—3 of FIG. 1; and

FIG. 4 is an enlarged sectional view in partial elevation showing the heater-electrode terminal subassembly of the sensor shown in FIGS. 1-3.

DESCRIPTION OF THE PREFERRED EMBODIMENTS

Reference is now made to the drawing hereof, which in FIGS. 1-3 shows a tubular metal shell 10, a solid electrolyte tube 12 that is closed at its bottom end, an electrode terminal member 14, and a heater 16. The electrolyte tube can be of stabilized zirconia, thoria, or the like. Electrode terminal member 14 has a central tubular portion 14a and a circumferential flange 14b at its lower end. Heater 16 is coaxially supported within terminal tube 14a, and forms a subassembly therewith in which heater 16 is electrically isolated from terminal member 14. The subassembly is specifically illustrated in FIG. 4, and will subsequently hereinafter be described in further detail.

Flat mica washer 20 is disposed on the upper surface of flange 14b. A ceramic ring 22 is concentrically disposed on mica washer 20 around terminal tube 14a. Ceramic ring 22 has an upward, decreasing taper 22a on its outer surface. A flared lower end 24 of a tubular, upper metal shield 26 nests on the tapered outer surface of ceramic ring 22. An annular metal gasket 28 surrounds the flared lower end 24 of shield 26. Below terminal flange 14b is an upper metal sealing ring 30, a circumferential flange 12a around the open upper end of the electrolyte tube 12, and metal lower sealing ring 32. A cup-shaped lower metal shield 34 is affixed to the lower end of shell 10, surrounding the otherwise exposed lower end of electrolyte tube 12. Lower metal shield 34 has louvers 36, for entry of exhaust gases. All of the aforementioned elements are coaxially aligned.

The sealing rings 28 and 30 can be of any soft metal, such as copper or nickel. The shell 10, metal shields 26 and 34, and at least the outer covering of heater 16 are made of metal which will withstand the conditions of sensor use, as for example at least stainless steel and preferably a nickel-based alloy. Ceramic ring 22 can be of any suitable ceramic, as for example alumina. Annular metal gasket 28 can be of soft steel.

On its outer surface, tubular metal shell 10 has circumferential threads 38 for mounting the sensor in an automobile exhaust pipe 42. Above threads 38 is an outer annular soft steel gasket 40. Above gasket 40 is a circumferential hexagonal array of surface flats 39, for tightening shell 10 in the exhaust pipe 42. If desired, the sensor could be alternatively mounted in an exhaust system manifold, tailpipe, or special parallel exhaust passage. On its inner surface, shell 10 has lower inward circumferential flange 44, providing an annular sloped shoulder 46. Shoulder 46 forms a tapered seat, on which lower sealing ring 32 is disposed. The upper end of shell 10 has an inward circumferential flange 48, formed by crimping or rolling over the soft steel gasket 28. Sloped shoulder 46 and upper flange 48 cooperate to concentrically clamp the aforementioned flanges, rings and washers within shell 10 in a predetermined fixed relationship.

The inner surface of shell 10 is generally cylindrical. Above shoulder 46 it has a larger diameter portion 50 and a smaller diameter portion 52. Portion 50 is of larger diameter to radially space shell 10 from the outer periphery of electrode terminal flange 14b, for electrical isolation purposes. Portion 52 is of a diameter only slightly larger than the outer diameter of the adjacent electrolyte tube flange 12a. The adjacent tube and shell diameters are sufficiently close to provide substantial coaxial alignment but not so close as to prevent easy assembly. About 0.040 inch or less nominal difference may be suitable.

Solid electrolyte tube 12 is tapered from its upper end to its closed lower end. The upper end has a larger diameter portion that forms a circumferential circular concentric flange 12a. Wall thickness on electrolyte tube 12 gradually decreases from flange 12a to the tube lower end. Flange 12a has a lower surface 56 which forms a sloped shoulder generally similar in slope to shoulder 46 of shell 10. Shoulders 46 and 56 cooperate, along with the shell reduced diameter portion 52, to coaxially align electrolyte tube 12 within shell 10. Lower metal sealing ring 32 between shoulders 46 and 56 provides a gas tight seal, and low resistance electrical communication between the surfaces.

A first porous thick film platinum electrode 58 fully covers the bottom inner surface of electrolyte tube 12. This inner electrode 58 serves as a reference electrode, in this case an air electrode for the sensor. A conductive strip-like coating 58a extends up the tube inner surface from electrode 58 to the open end of the tube 12, where it intersects with conductive coating 58b on the end face of electrolyte tube 12. Conductive coating 58b can merely be a strip across the end face of electrolyte tube 12 or be a continuous circumferential coating. The platinum electrode 58 and conductive coatings 58a and 58b can be a continuous layer formed by brushing on a platinum paste and then firing it, as is usual.

A second porous thick film platinum electrode 60 covers the entire outer surface of tube 12, including the shoulder 56, below flange 12a. This outer electrode 60 serves as the exhaust gas electrode for the sensor. Outer platinum electrode 60 can be formed in the same manner as inner electrode 58. However, it may be more desirable to apply it by evaporation, sputtering or other such techniques. Outer electrode 60 is in low resistance electrical contact with shell 10 through the lower soft metal gasket 32. Hence, this electrode is also in low resistance electrical communication with upper shield 26 and exhaust pipe 42. A porous ceramic coating 62 of alumina, spinel, or the like preferably covers the outer electrode 60 below electrolyte tube shoulder 56.

The upper end of electrolyte tube 12 is chamfered on its periphery, forming a sloped shoulder 64. The outer periphery of upper sealing ring 30 has a complementary contour. The inner periphery of sealing ring 30 has an axial flange 30a to facilitate concentric seating of sealing ring 30 on the open end face of tube 12. Inner electrode 58 and electrode terminal 14 are in low resistance electrical contact through platinum strip 58a, conductive coating 58b and sealing ring 30. Electrode terminal flange 14b has a sloped shoulder 66 on the outer periphery of its lower face, at least generally corresponding to sealing ring 30 and electrolyte tube shoulder 64. Sloped shoulders 64 and 66 cooperate to coaxially align electrode terminal 14 with electrolyte tube 12.

The upper surface of flange 14b is normal to the axis of terminal tube 14a. Also, the lower end face of ceramic ring 22 is normal to the longitudinal axis of coaxial passage 68 extending through the ceramic ring. The tapered outer surface 22a of ceramic ring 22 coacts with the adjacent metal gasket 28 and shell flange 48 to not only clamp the components together but also coaxially align ceramic ring 22 and its passage 68 within shell 10. Passage 68 has a diameter about 0.040 inch, preferably about 0.005–0.01 inch larger than the outer diameter of terminal tube 14a, enhancing coaxial alignment of terminal 14 and the subassembly of which it is a part. As can be seen, the taper 22a on ceramic ring 22 is gradual at its upper end to enhance coaxial alignment and more abrupt at its lower end to enhance the clamping effect. Since flared lower end 24 of upper metal shield 26 conforms to the taper 22a of the ceramic ring and nests thereon under gasket 28, shield 26 is also coaxially aligned.

The upper end of shield 26 is open and radially spaced from heater 16. Shield 26 is, therefore, electrically isolated from heater 16. While not shown, shield 26 can have a conformation above ceramic ring 22 to retain an upper insulating spacer in place and help retain a terminal connector that may be attached. As mentioned, shield 26 is in low resistance electrical communication with outer electrode 60 on electrolyte tube 12. Shield 26 can, therefore, serve as a ground connection, if desired, instead of exhaust pipe 42. To insure low resistance connection, an electroplated coating 70 of silver or the like can be provided on the upper end of shield 26.

The open upper end of shield 26 provides an aperture 72 through which ambient air can enter the interior of the sensor. Air entering the sensor through aperture 72 passes down through shield 26 to the narrow generally annular passage 68 between ceramic ring 22 and electrode terminal tubular portion 14a. Air entering annular passage 68 passes downwardly to aperture 74 in the lower wall of tube 14a, and through aperture 74 to a lower narrow generally annular passage 76 between heater 16 and the lower end of terminal tube 14a. A spacing of about 0.005–0.01 inch between the inner diameter of the tube 14a and the outer diameter of heater 16 is adequate to provide the lower annular passage 76. Air passes through passage 76 into the interior of electrolyte tube 12, where it contacts the inner electrode 58. Thus, the interior of the electrolyte tube 12 communicates with outside air through a baffled passage, protecting it from particulate contaminants, water splash, etc. It should also be mentioned that passages 68 and 76 are formed by merely appropriately dimensioning the respective parts with a generous manufacturing clearance. No intricate machining is required and assembly is simple. Hence, passage 68 of ceramic ring 22 can coact in coaxial alignment of heater-terminal subassembly. Passage 68 can be quite narrow, since only a very small rate of air flow is necessary during sensor operation. The rate of air flow resulting from air leakage due only to normal manufacturing tolerances, e.g. 0.003–0.005 inch minimum clearance, may be all that is necessary to provide an adequate air flow path.

As can be seen better by also referring to FIG. 4, heater 16 is coaxially bonded within electrode terminal tube 14a by a fused glass 78. By fused glass we mean a body of glass that has been melted and resolidified in place, whereby the resolidified glass body adheres to surfaces it contacts. Heater 16 includes a tubular outer metal sheath 80 closed at its lower end within which a coaxial helical heating coil 82 is disposed. The lower end of coil 82 is welded to the bottom of sheath 80. The upper end of coil 82 is welded to a coaxial inner rod 84. Coil 82 and rod 84 are spaced from outer sheath 80 by ceramic insulation 86 as for example powdered magnesia. If desired, the open upper end 88 of sheath 80 can be closed by means of a sealing ring (not shown) of nonconductive material, as for example silicone rubber. The upper end 88 of sheath 80 has a silver coating at 90, as does the adjacent inner heater rod 84 at 92, to insure low resistance electrical connections thereat. Heater 16 is therefore actuated by applying an electrical potential across sheath 80 and rod 84. If desired, heaters made in accordance with the teachings of U.S. Pat. No. 2,898,571 Moule et al and U.S. Pat. No. 3,252,122 Baxter can be used.

As mentioned, heater 16 is coaxially bonded within electrode terminal tubular portion 14a by fused glass 78. The outer surface of heater 16 is knurled at 94 to enhance bonding of the fused glass 78. Above and below fused glass 78, heater 16 is respectively spaced from electrode terminal tubular portion 14a by an upper ceramic sleeve 96 and a lower ceramic sleeve 98. As can be seen, lower ceramic sleeve 98 is supported on a circumferential shoulder 100 on the inner surface of terminal tubular portion 14a. Ceramic sleeves 96 and 98 radially space heater 16 from the inner surface of electrode terminal tube 14a along its entire length. This not only thermally separates heater 16 and terminal tube 14a but electrically isolates them. Thus, less heat is lost from the sensor during heating and the sensor can be continuously heated during sensing. Fused glass 78 initially was a cylindrical body slightly longer than the spacing between ceramic sleeves 96 and 98 shown in the drawing. The glass cylinder and sleeves 96 and 98 were assembled in tube 14a, with sleeve 96 projecting slightly beyond the end face 102 of terminal tubular portion 14a. Heater 16 was properly inserted within them in proper axial displacement with respect to the ends of tube 14a. The glass cylinder was then melted and upper ceramic sleeve 96 moved into tube 14a to the position shown in the drawing. As a result, the molten glass completely filled an annular region between knurled portion 94 and the radially adjacent terminal tubular portion 14a. Concurrently, portions of the molten glass also were axially displaced a short distance along the inner and outer surfaces of the adjacent ends of the ceramic sleeves. Along this distance, the molten glass filled the space between the sleeves and the heater 16 and the tube 14a at least at the sleeve inner ends. The molten glass was then cooled, so that it solidified and bonded to heater 16, terminal tubular portion 14a, and ceramic sleeves 96 and 98. The glass also provides a seal. Its composition is not critical. Any glass can be used that melts at a temperature above the highest operating temperature expected for the device, usually about 700° C., and below a temperature deleteriously affecting the heater or terminal materials such as their melting or sintering temperatures. A glass melting at about 1000° C. can be used.

Tube 14a is normal to the upper surface of flange 14b. For best results, tube 14a is generally at least about 5 times longer, and preferably about 10 to 15 times or more longer than the dimension of its inner diameter. Since tube 14a has considerable length, ceramic sleeves 96 and 98 can be made somewhat loosely fitting within tube 14a to ease assembly. Nonetheless, they can effectively precisely align heater 16 within the tube 14b. However, even if somewhat loosely fitting, sleeves 96 and 98 are rigidly held in place by the fused glass 78 in the finished subassembly shown in drawings 1 and 4. Thus, the axis of heater 16 is maintained substantially normal to the upper surface of electrode terminal flange 14b.

The upper end of terminal tube 14a is silver plated at 104, to enhance a low resistance connection. As can be seen, all terminals for the sensor are coaxial, with progressively larger silver plated terminal connections at 92, 90, 104 and 70. The innermost two terminal connections 92 and 90 are for applying a heating voltage across heater 16. The outermost two terminal connections 104 and 70 are for obtaining an output voltage from platinum electrodes 58 and 60 on the inner and outer faces of solid electrolyte tube 12.

The embodiments of the invention in which an exclusive property or privilege is claimed are defined as follows:

1. In a galvanic exhaust gas sensor having a solid electrolyte member, a subassembly comprising a heater and an outwardly flanged terminal tube for said electrolyte member, an inwardly flanged tubular metal shell surrounding said electrolyte member and heater-terminal tube subassembly, and means coacting with said flanges for holding said member, subassembly and shell in a fixed predetermined relationship, the improvement wherein said heater-terminal tube subassembly includes at least one ceramic sleeve coaxially disposed within the terminal tube and extending along a substantial length thereof, an elongated heater disposed within the ceramic sleeve, and a vitreous material bonding said heater, sleeve and terminal tube together as a subassembly in predetermined disposition with respect to said electrolyte member, whereby said vitreous material supports said heater on said terminal tube, said ceramic sleeve aligns said heater within said terminal tube, and the heater and terminal tube are thermally separated and electrically isolated.

2. In a galvanic exhaust gas sensor having a circular solid electrolyte member, a subassembly comprising a heater and an outward circumferentially flanged concentric terminal tube for said electrolyte member, an inwardly flanged tubular metal shell surrounding said electrolyte member and heater-terminal tube subassembly, and means coacting with said flanges for coaxially retaining said member, subassembly and shell in a fixed predetermined relationship, the improvement wherein said terminal tube is over five times longer than its inner diameter, at least two axially displaced ceramic sleeves are coaxially disposed within said terminal tube and extend along a substantial length thereof, an elongated heater axially extends through said sleeves and is precisely coaxially aligned with said terminal tube thereby, and a vitreous material bonds said heater, said tube and adjacent inner ends of said sleeves together in a subassembly with said heater in fixed predetermined disposition with respect to said electrolyte member, whereby said vitreous material supports said aligned heater on said terminal tube and cooperates with said ceramic sleeves to electrically isolate and thermally separate said heater from said terminal tube.

3. In a galvanic exhaust gas sensor having a closed ended tubular solid electrolyte member, a subassembly comprising a heater and an outward circumferentially flanged concentric terminal tube for said electrolyte member, an inwardly flanged tubular metal shell surrounding said electrolyte member and heater-terminal tube subassembly, and means coacting with said flanges for coaxially retaining said member, subassembly and shell in a fixed predetermined relationship, the improvement wherein said terminal tube is over ten times longer than its inner diameter, at least two axially displaced ceramic sleeves are coaxially disposed within said terminal tube and extend along substantially the entire length thereof, an elongated heater axially extends through said sleeves and is thereby precisely coaxially aligned with and radially spaced from said terminal tube, said heater having a portion axially displaced outwardly from said terminal tube and in predetermined disposition within said electrolyte tube, a glassy material bonds said heater, said tube and adjacent inner ends of said sleeves together in a subassembly effective to insulatingly support said heater in said terminal tube in fixed predetermined disposition with respect to said electrolyte member, and said subassembly provides a tortuous restricted flow path for entry of ambient air into said electrolyte tube.

4. In a generally cylindrical galvanic exhaust gas sensor having a solid electrolyte tube closed at one end and an air reference electrode on its inner face, an outwardly flanged concentric electrode terminal tube, a heater for said electrolyte tube supported in subassembly in said terminal tube, an inwardly flanged tubular metal shell surrounding said tubes and heater, and means coacting with said flanges for coaxially retaining said tubes, heater and shell in a fixed predetermined coaxial relationship, the improvement wherein said terminal tube has a length more than about 10 times its inner diameter to enhance coaxial alignment of the heater within the terminal tube, the terminal tube has an interior shoulder adjacent its outward flange, at least two axially displaced substantially equal diameter ceramic sleeves are coaxially disposed within and extend along a substantial length of said terminal tube, an end on one of said ceramic sleeves abuts said shoulder, an elongated heater having coaxial terminals at one end and a resistance heating element at the other end is axially disposed within said ceramic sleeves, said coaxial sleeves radially space said heater from said terminal tube, and coaxially align it therewith, said other heater end is axially displaced a predetermined distance outward from one end of said terminal tube for a predetermined heating relationship with said electrolyte tube, the one heater end is axially displaced outward from the other terminal tube end to permit separate coaxial connections to said heater and terminal tube, a glassy material bonds the heater and the terminal tube together between adjacent inner ends of the ceramic sleeves to form a subassembly in which said heater is electrically and thermally isolated from said terminal tube and yet sealed therewithin, and said terminal tube has an air inlet for said reference electrode interconnecting two narrow annular coaxial air flow passages by which said reference electrode is protected from contamination.

5. In a method for assembling a heated galvanic exhaust gas sensor having a solid electrolyte member, an outwardly flanged concentric tubular terminal for a reference electrode on one face of said electrolyte member, an inwardly flanged tubular metal shell surrounding said electrolyte member and said terminal, and means coacting with said terminal and shell flanges for biasing said element, terminal and shell together in a fixed predetermined relationship, the improvement comprising coaxially disposing at least one ceramic sleeve within said tubular terminal, coaxially disposing heater terminals within said sleeves, which heater terminals have a heating coil affixed therebetween, vitreously bonding said sleeve, tubular terminal and heater terminals together effective to insulatingly support said heater terminals and heating coil on said tubular terminal and thereby form a subassembly having an electrically isolated heating coil in fixed predetermined relationship with respect to said electrolyte member and said shell, and assembling said subassembly with said electrolyte member and said shell wherein alignment of said tubular terminal also aligns said heating coil with said electrolyte member in a predetermined spaced disposition.

6. In a method for assembling a heated galvanic exhaust gas sensor having a solid electrolyte member, an outwardly flanged concentric tubular terminal for a reference electrode on one face of said electrolyte member, a heater in subassembly with said terminal, an inwardly flanged tubular metal shell surrounding said electrolyte member and said heater-terminal subassembly, and means coacting with said terminal and shell flanges for biasing said element, heater-terminal subassembly and shell together in a fixed predetermined relationship, the improvement comprising coaxially disposing two ceramic sleeves and a glass cylinder within said terminal, said glass cylinder spacing apart facing ends of said sleeves, disposing a coaxial heater within said sleeves and cylinder in predetermined relationship with respect to said terminal, melting and resolidifying said cylinder glass to bond it to said heater, terminal and facing sleeve ends and form a subassembly in which said heater is electrically isolated and thermally separated from said terminal, said subassembly having a fixed predetermined relationship with respect to said electrolyte member and said shell, and assembling said subassembly with said electrolyte member and said shell wherein alignment of said terminal also aligns said heater with said electrolyte member in a predetermined spaced disposition.

* * * * *